United States Patent
Reed et al.

(10) Patent No.: US 6,182,494 B1
(45) Date of Patent: Feb. 6, 2001

(54) METHOD FOR ADJUSTMENT OF TRANSDUCER POSITION TO COMPENSATE FOR ULTRASONIC TESTING BEAM ALIGNMENT ERRORS

(75) Inventors: Francis Alexander Reed, Scotia; Thomas James Batzinger, Burnt Hills, both of NY (US)

(73) Assignee: General Electric Company, Schenectady, NY (US)

( * ) Notice: Under 35 U.S.C. 154(b), the term of this patent shall be extended for 0 days.

(21) Appl. No.: 09/406,120

(22) Filed: Sep. 27, 1999

(51) Int. Cl.[7] .................................................. G01N 27/04
(52) U.S. Cl. .............................. 73/1.83; 73/1.84; 73/1.86
(58) Field of Search ............................... 72/1.82–1.84, 72/1.86, 1.79, 1.81; 367/13

(56) References Cited

U.S. PATENT DOCUMENTS 4,170,891 * 10/1979 Elsner .................................. 73/1.83
5,381,383 * 1/1995 Burfeindt .

* cited by examiner

Primary Examiner—Robert Raevis

(57) ABSTRACT

A transducer position adjustment method, performed to compensate for initial ultrasonic beam alignment error, includes the steps of providing a manipulator of an ultrasonic immersion testing system having a pointing direction and supporting a transducer generating an ultrasonic beam, providing a calibration body defining a target thereon, immersing the transducer of the manipulator and the calibration body in a coupling fluid in an immersion tank of the system, setting the manipulator initially at a first position such that the pointing direction of the manipulator is aligned with the calibration body target at known coordinates, and adjusting the manipulator subsequently to a second position such that the ultrasonic beam of the transducer is brought into alignment with the calibration body target at the known coordinates for initiating an inspection of a test object after replacing the calibration body with the test object.

16 Claims, 4 Drawing Sheets

METHOD FOR ADJUSTMENT OF TRANSDUCER POSITION TO COMPENSATE FOR ULTRASONIC TESTING BEAM ALIGNMENT ERRORS

BACKGROUND OF THE INVENTION

The present invention generally relates to ultrasonic testing of objects and, more particularly, is concerned with a method for adjustment of transducer position to compensate for ultrasonic testing beam alignment errors.

As depicted diagrammatically in FIG. 1, a prior art ultrasonic immersion testing system 10 typically involves the use of an immersion tank 12 for holding an object 14 immersed in a coupling fluid 16 and a manipulator 18 positioned on the tank 12 such that the pointing direction 20 of the manipulator 18 intersects the object 14 at known coordinates. The manipulator 18 mounts a transducer 22 which also is immersed in the coupling fluid 16 and generates an ultrasonic beam 24 toward the object 14 to be inspected or tested.

Ultrasonic immersion testing requires that the ultrasonic beam 24 intersect a surface 14a of the test object 14 at a defined angle. For 20 most volumetric inspections, the ultrasonic beam 24 should be parallel to a normal vector 26 from the object surface 14a at the point of intersection 28 of the beam 24 with the surface 14a. However, in most ultrasonic immersion systems, small angle errors E will be present between the positions of the manipulator 18 and transducer 22 of the system 10 causing the pointing direction 20 of the manipulator 18 and the direction of the ultrasonic beam 24 from the transducer 22 to be offset or diverge from one another such that the ultrasonic beam 24 will not be parallel with the normal vector 26 at the point of intersection 28 of the ultrasonic beam 24 with the surface 14a of the object 14.

Ultrasonic immersion systems capable of scanning complex shape objects use information collected from computer-generated descriptions of the object or from "teach and learn" scanner applications to orient the transducer. These systems typically use simplified geometric algorithms to position the transducer for evaluation of the object. These systems, however, cannot correct for position and angle offsets that are associated with the transducer and the manipulator. These offsets can lead to errors in the positioning and orienting of the transducer which can reduce the detection capability of the ultrasonic evaluation.

The small errors in the transducer alignment relative to the manipulator pointing direction can lead to larger angle errors between the ultrasonic beam and the surface normal vector. The significance of the positioning errors are increased by the surface curvature of complex shape objects. Errors in the location of intersection between the ultrasonic beam and the surface of the object will lead to increased errors in the alignment of the ultrasonic beam relative to the surface normal vector at the point of incidence.

This additional alignment error limits the use of contour following methods on complex shape objects. Objects with small radii of-curvature will have larger angle alignment errors for the same beam position errors. To use contour following methods to scan complex shape objects, these positioning errors caused by misalignment of the ultrasonic beam must be minimized.

Consequently, a need exists for an innovation which will provide a solution to the aforementioned misalignment error problem without introducing any new problems in place thereof.

BRIEF SUMMARY OF THE INVENTION

The present invention provides a transducer position adjustment method designed to satisfy the aforementioned need. The adjustment method of the present invention corrects the transducer position so as to thereby compensate for ultrasonic beam translation and rotation alignment errors. The method requires no modification in the computer software and geometric algorithms used by the ultrasonic immersion system. Therefore, the method can be used to compensate for alignment errors with any generic contour-following ultrasonic testing scanner.

In an embodiment of the present invention, therefore, a method is provided for adjustment of transducer position relative to an object to compensate for ultrasonic testing beam alignment errors. The transducer position adjustment method comprises the steps of providing a manipulator of an ultrasonic immersion testing system having a pointing direction and supporting a transducer generating an ultrasonic beam, providing a calibration body defining a target thereon, immersing the transducer of the manipulator and the calibration body in a coupling fluid in an immersion tank of the ultrasonic immersion testing system, setting the manipulator initially at a first position such that the pointing direction of the manipulator is aligned with the target of the calibration body at known coordinates, and adjusting the manipulator subsequently to a second position such that the ultrasonic beam of the transducer is br ought into alignment with the target of the calibration body at the known coordinates for initiating an inspection of a test object after replacing the calibration body with the test object.

More particularly, the calibration body is provided with a generally block-like configuration and a top surface. The target of the calibration body is in the form of a recess defined in the bottom surface of the calibration body. The recess of the calibration body has a flat bottom. The setting of the manipulator includes defining the first position by a first angle and a second angle. The first angle is defined between the manipulator pointing direction and a positive Z axis of the ultrasonic immersion testing system. The second angle is defined between the manipulator pointing direction and an X axis in the plane of the X axis and a Y axis of the ultrasonic immersion testing system. The adjusting of the manipulator includes defining the second position by the first angle and the second angle and scanning the calibration body with the ultrasonic beam of the transducer to align the ultrasonic beam of the transducer with the target of the calibration body.

DETAILED DESCRIPTION OF THE INVENTION

Figure 1:
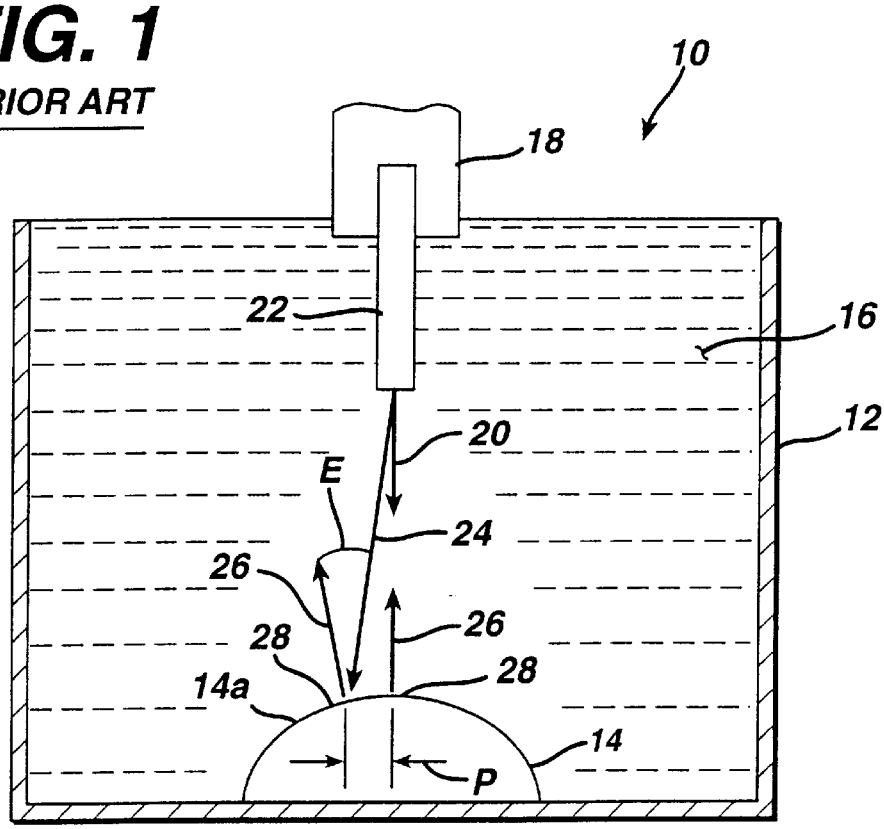
FIG. 1 is a diagrammatic view of a prior art ultrasonic immersion testing system wherein a manipulator mounts and points a transducer toward an object to be inspected and produces an angle error between the pointing direction of the manipulator and the direction of an ultrasonic beam generated by the transducer relative to a surface normal vector of the test object.
Figure 2:
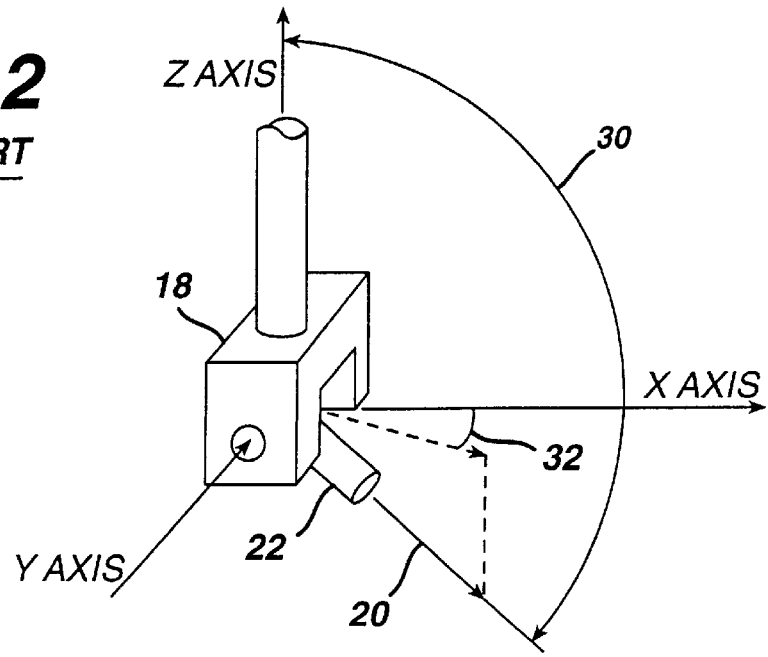
FIG. 2 is a diagrammatic view of the manipulator of the system, showing the rotation coordinates of the manipulator relative to a positive Z axis of the system.

Referring now to the drawings, and particularly to FIG. 2, there is diagrammatically illustrated the manipulator 18 which is used in the prior art ultrasonic immersion testing system 10. The manipulator 18 is positioned on the immersion tank 12 (see FIG. 1) of the system 10 which is at least partially filled with the coupling fluid 16 (seen FIG. 1), which is any suitable well-known liquid used for this purpose. The manipulator 18 is positioned on the tank 10 at known coordinates of an X axis, a Y axis and a Z axis of the system 10. The transducer 22 supported by the manipulator 18 emits an ultrasonic beam 24 toward the test object 14 (see FIG. 1) to evaluate the test object 14. The transducer 22 and the test object 14 are immersed in the coupling fluid 16 in the tank 12 of the system 10.

The ultrasonic immersion testing system 10 relies on known computer software and geometric algorithms which are based on the assumption that, relative to known coordinates of the manipulator 18, the ultrasonic beam 24 is oriented in a direction defined by two angles, a first angle 30 and a second angle 32. The first angle 30 is defined between the pointing direction 20 of the manipulator 18 and the positive Z axis of the system 10. The second angle 32 is defined between the pointing direction 20 of the manipulator and the X axis of the system 10 in the plane of the X and Y axes of the system 10. The manipulator pointing direction 20 intersects the test object 14 at the known coordinates of the manipulator 18 for the given system 10. The ultrasonic beam 24 must intersect the manipulator pointing direction 20 at the surface 14a of the test object 14 at a defined angle.

For most volumetric inspections, the ultrasonic beam 24 should be parallel to the normal vector 26 from the test object surface 14a at the point of intersection 28 of the ultrasonic beam 24 with the test object surface 14a. In most ultrasonic immersion testing systems, small errors will be present between the positions of the manipulator 18 and the transducer 22 causing the pointing direction 20 of the manipulator 18 and the direction of the ultrasonic beam 24 to be offset or diverge from one another such that the ultrasonic beam 24 will not be parallel with the normal vector 26 at the point of intersection 28 of the ultrasonic beam 24 with the test object surface 14a. This offset or angle error is indicated at E (see FIG. 1). There is also a position error P 28 on the object surface 14a which is associated with the angle error E.

Figure 3:
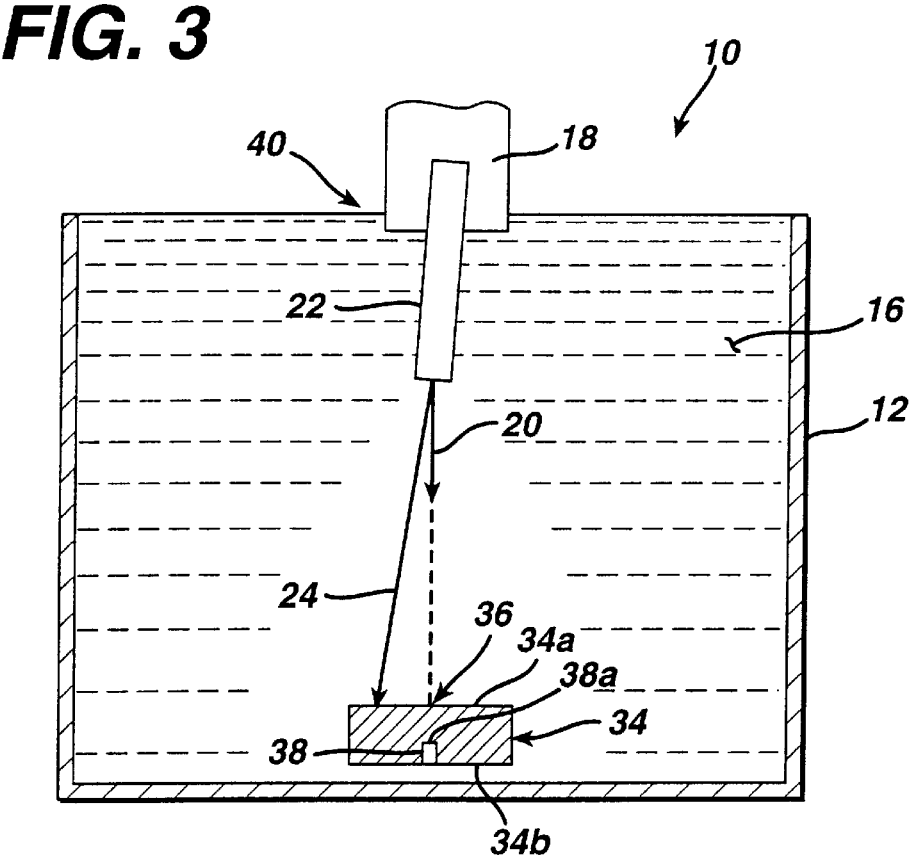
FIG. 3 is a diagrammatic view of an early step of a transducer position adjustment method of the present invention wherein the position of the manipulator and transducer therewith are initially set such that the manipulator pointing direction is aligned with a target of a calibration body.
Figure 4:
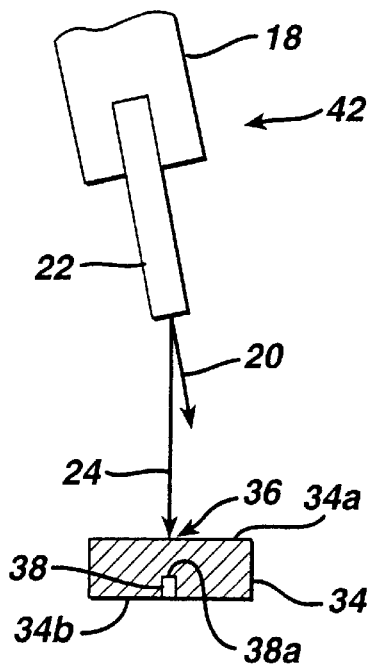
FIG. 4 is a diagrammatic view of a subsequent step of the transducer position adjustment method wherein the position of the manipulator and the transducer therewith are adjusted such that the ultrasonic beam direction is brought into alignment with the target of the calibration body.

Referring now to FIGS. 3 and 4, there is illustrated the steps of the method of the present invention where the position of the transducer 22 is adjusted to compensate for the alignment errors of the ultrasonic beam 24. The method employs the above-described manipulator 18 of the prior art ultrasonic immersion testing system 10 which has the pointing direction 20 defined at known coordinates of the system 10. The manipulator 18 supports the transducer 22 which generates the ultrasonic beam 24.

In order to facilitate correction of the inherent misalignment of the ultrasonic beam 24 with the normal vector 26 at the point of intersection 28 of the ultrasonic beam 24 with the surface 14a of a test object 14 as discussed above with reference to FIG. 1, the transducer position adjustment method employs a calibration body 34 which has a target 36 thereon. The transducer 22 and calibration body 34 are both immersed in the coupling fluid 16 in the tank 12 of the system 10 such that the ultrasonic beam 24 can be effectively transmitted from the transducer 24 to the calibration body 34 for inspecting the calibration body 34. The calibration body 34 is preferably block-like and may have a rectangular shape, although it can have other shapes. The calibration body 34 also has a top surface 34a facing toward the transducer 22 and the target 36 on the calibration body 34 is preferably in the form of a recess 38 defined centrally in the bottom surface 34b. The calibration body 34 is located in the tank 12 such that recess 38 thereon is located at the known coordinates of the system 10. The recess 38 can be of a generally rectangular configuration and has a flat bottom 38a.

The manipulator 18 is initially set at a first position 40, as seen in FIG. 3, such that its pointing direction 20 is aligned with the target 36 at the known coordinates. The known coordinates of the first position 40 of the manipulator 18 are defined by the aforementioned first and second angles 30, 32 shown in FIG. 2. The manipulator 18 is subsequently adjusted to a second position 42, as seen in FIG. 4, such that the ultrasonic beam 24 of the transducer 22 is brought into alignment with the target 36 of the calibration body 34 at the known coordinates. Thus, the coordinates of the second position 42 are then defined by the aforementioned first and second angles 30, 32. The manipulator 18 is adjusted from the first position 40 to the second position 42 by scanning the calibration body 34 with the ultrasonic beam 24 of the transducer 22 until the ultrasonic beam 24 is brought into alignment with the target 36. A signal (not shown) or echo reflected from the calibration body 34 will show the presence of the target 36 upon the ultrasonic beam 24 impacting the recess 38 on the calibration body 34. The signal is different when the ultrasonic beam 24 is within the recess 38 than when the ultrasonic beam 24 is outside of the recess 38. In such manner, the location of the recess 38 can be monitored and determined in the process of scanning the calibration body 34. Once the adjustment of the transducer 22 so as to compensate for the alignment errors is completed, the inspection of the test object 14 can be initiated after the calibration body 34 is replaced with the test object 14.

Figure 5:
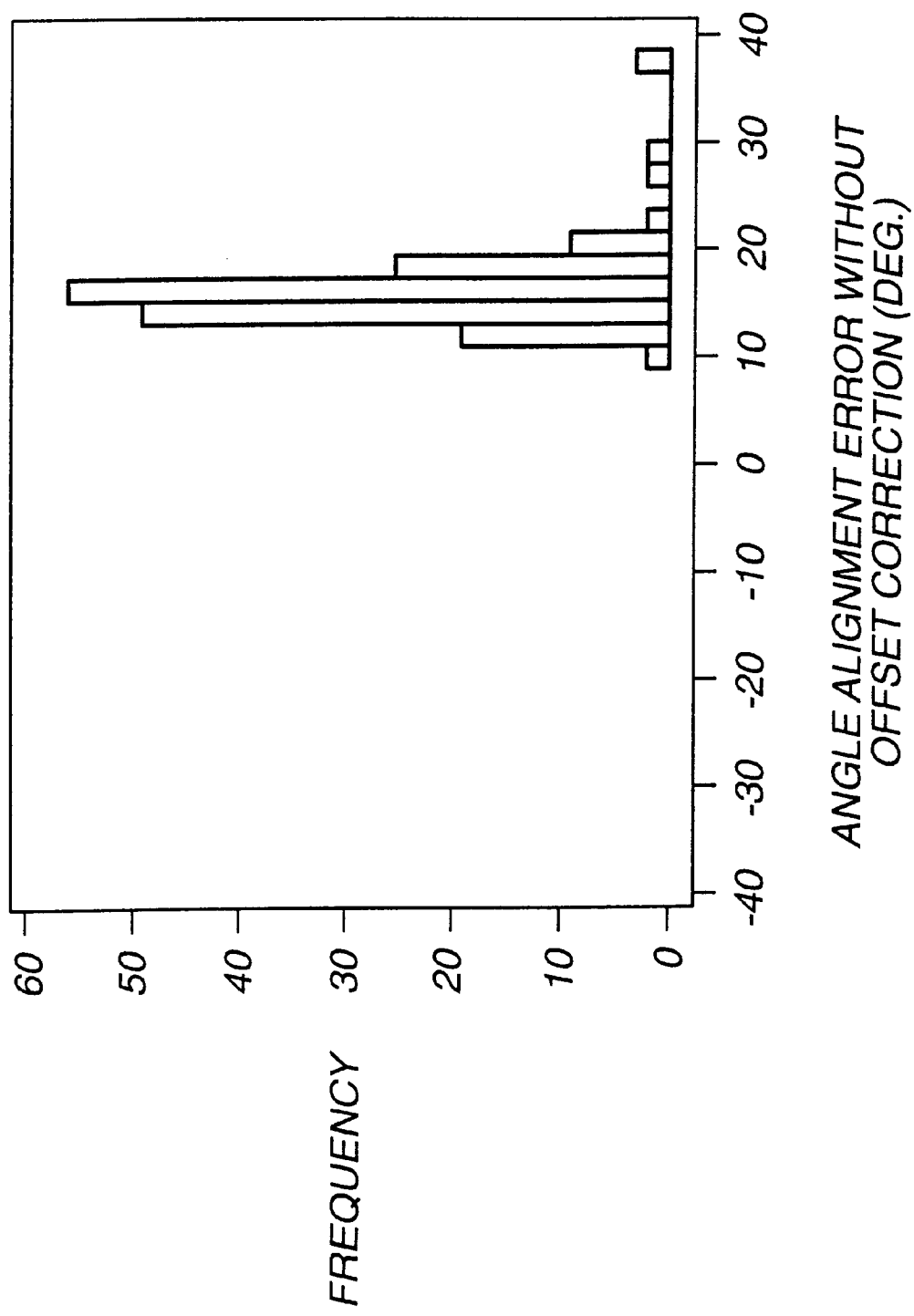
FIG. 5 is a histogram of a large alignment error that exists before manipulator position adjustment or correction.
Figure 6:
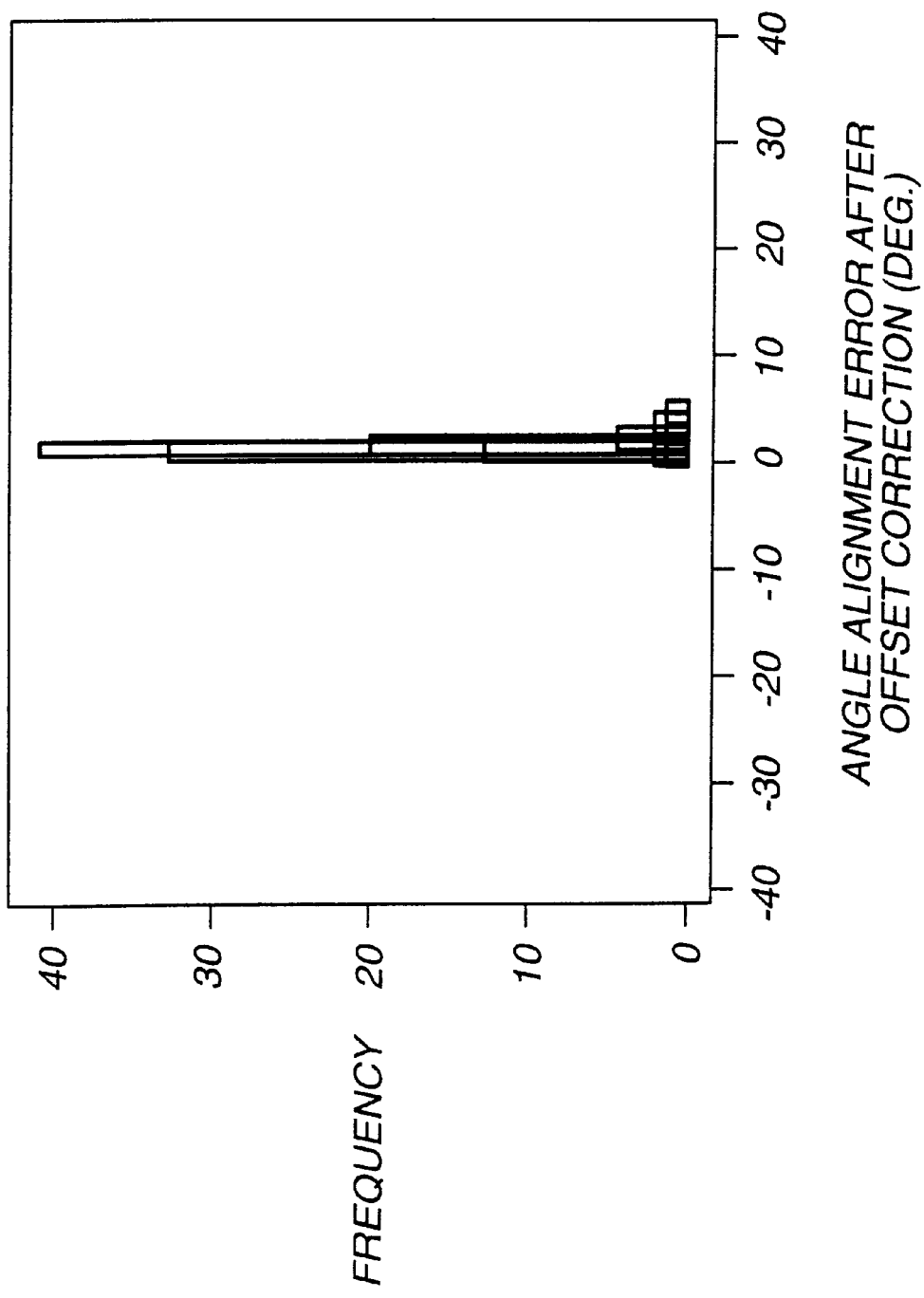
FIG. 6 is a histogram of a small alignment error that exists after manipulator position adjustment or correction.

Referring now to FIGS. 5 and 6, histograms are shown which display the difference between the alignment errors with and without employment of the transducer position adjustment method of the present invention. The leading edge of a gas turbine nozzle was scanned using standard manipulator angle assignments. The pointing direction of the manipulator was determined. The actual normal vector direction was then found at the actual ultrasonic beam intersection point on the object surface. The difference in the two directions in the plane of the X and Y axes was then calculated for each scan point. In FIG. 5, a histogram of the angle difference in degrees is shown. The average angle error between the direction that the transducer is pointed and the normal vector is approximately 16 degrees. This angle error is due to an ultrasonic beam position error of approximately 0.13 inches at the object surface. Thus, a large alignment error is shown in FIG. 5 to exist before carrying out the transducer (or manipulator) position adjustment or correction.

The method of the present invention as described above was then performed and the same object was scanned using the new angle direction assignments. The angle difference between the normal vector and the pointing direction of the manipulator was again calculated. In FIG. 6, a histogram of the angle difference in degrees is shown. The average angle error between the direction that the transducer is pointed and the normal vector is approximately 1 degree. Improvement of the alignment of the ultrasonic beam is thus apparent from the histograms of FIGS. 5 and 6. Thus, a small alignment error is shown in FIG. 6 existing exists after manipulator position adjustment or correction. Acceptable volumetric scans can be performed using this correction.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

What is claimed is:

1. A method for adjustment of transducer position to compensate for ultrasonic testing beam alignment errors, the method comprising the steps of:
   providing a manipulator of an ultrasonic immersion testing system having a pointing direction and supporting a transducer generating an ultrasonic beam;
   providing a calibration body defining a target thereon;
   immersing the transducer of the manipulator and the calibration body in a coupling fluid in an immersion tank of the ultrasonic immersion testing system;
   setting the manipulator initially at a first position such that the pointing direction of the manipulator is aligned with the target of the calibration body at known coordinates; and
   adjusting the manipulator subsequently to a second position such that the ultrasonic beam of the transducer is brought into alignment with the target of the calibration body at the known coordinates for initiating an inspection of a test object after replacing the calibration body with the test object.

2. The method of claim 1 in which the calibration body is provided with a generally block-like configuration.

3. The method of claim 1 in which the calibration body is provided with a top surface and a bottom surface and the target of the calibration body is provided in the form of a recess defined in the bottom surface of the calibration body.

4. The method of claim 3 in which the recess of the calibration body is provided with a generally flat bottom.

5. The method of claim 1 in which the setting of the manipulator includes defining the first position by a first angle and a second angle, the first angle being defined between the manipulator pointing direction and a positive Z axis of the ultrasonic immersion testing system, the second angle being defined between the manipulator pointing direction and an X axis of the ultrasonic immersion testing system in the plane of the X axis and a Y axis of the ultrasonic immersion testing system.

6. The method of claim 1 in which the adjusting of the manipulator includes defining the second position by a first angle and a second angle, the first angle being defined between the manipulator pointing direction and a positive Z axis of the ultrasonic immersion testing system, the second angle being defined between the manipulator pointing direction and an X axis of the ultrasonic immersion testing system in the plane of the X axis and a Y axis of the ultrasonic immersion testing system.

7. The method of claim 1 in which the adjusting of the manipulator includes scanning the calibration body with the ultrasonic beam of the transducer to align the ultrasonic beam of the transducer with the target of the calibration body.

8. A method for adjustment of transducer position to compensate for ultrasonic testing beam alignment errors, the method comprising the steps of:
   providing a manipulator of an ultrasonic immersion testing system having a pointing direction and supporting a transducer generating an ultrasonic beam;
   providing a calibration body having a top surface, a bottom surface and a target in the form of a recess defined in the bottom surface of the calibration body, the recess having a flat bottom;
   immersing the transducer of the manipulator and the calibration body in a coupling fluid in an immersion tank of the ultrasonic immersion testing system;
   setting the manipulator initially at a first position such that the pointing direction of the manipulator is aligned with the target of the calibration body at known coordinates; and
   adjusting the manipulator subsequently to a second position by scanning the calibration body with the ultrasonic beam of the transducer to align the ultrasonic beam of the transducer with the target of the calibration body at the known coordinates for initiating an inspection of a test object after replacing the calibration body with the test object.

9. The method of claim 8 in which the calibration body is provided with a generally block-like configuration.

10. The method of claim 8 in which the setting of the manipulator step includes defining the first position by a first angle and a second angle, the first angle being defined between the manipulator pointing direction and a positive Z axis of the ultrasonic immersion testing system, the second angle being defined between the manipulator pointing direction and an X axis of the ultrasonic immersion testing system in the plane of the X axis and a Y axis of the ultrasonic immersion testing system.

11. The method of claim 8 in which the adjusting of the manipulator step includes defining the second position by a first angle and a second angle, the first angle being defined between the manipulator pointing direction and a positive Z axis of the ultrasonic immersion testing system, the second angle being defined between the manipulator pointing direction and an X axis of the ultrasonic immersion testing system in the plane of the X axis and a Y axis of the ultrasonic immersion testing system.

12. A method for adjustment of transducer position to compensate for ultrasonic testing beam alignment errors, the method comprising the steps of:
   providing a manipulator of an ultrasonic immersion testing system having a pointing direction and supporting a transducer generating an ultrasonic beam;
   providing a calibration body defining a target thereon;
   immersing the transducer of the manipulator and the calibration body in a coupling fluid in an immersion tank of the ultrasonic immersion testing system;
   setting the manipulator initially at a first position such that the pointing direction of the manipulator is aligned with the target of the calibration body at known coordinates, the first position being defined by a first angle and a second angle, the first angle being defined between the manipulator pointing direction and a positive Z axis of the ultrasonic immersion testing system, the second angle being defined between the manipulator pointing direction and an X axis of the ultrasonic immersion testing system in the plane of the X axis and a Y axis of the ultrasonic immersion testing system; and adjusting the manipulator subsequently to a second position such that the ultrasonic beam of the transducer brought into alignment with the target of the calibration body at the known coordinates for initiating an inspection of a test object after replacing the calibration body with the test object, the second position now being defined by the first angle and the second angle.

13. The method of claim 12 in which the calibration body is provided with a generally block-like configuration.

14. The method of claim 12 in which the calibration body is provided with a top surface and a bottom surface and the target of the calibration body is provided in the form of a recess defined in the bottom surface of the calibration body.

15. The method of claim 14 in which the recess of the calibration body is provided with a generally flat bottom.

16. The method of claim 12 in which the adjusting of the manipulator includes scanning the calibration body with the ultrasonic beam of the transducer to align the ultrasonic beam of the transducer with the target of the calibration body.

* * * * *